US008683635B2

(12) United States Patent
Jungnickel et al.

(10) Patent No.: US 8,683,635 B2
(45) Date of Patent: Apr. 1, 2014

(54) ELECTRIC TOOTHBRUSH

(75) Inventors: Uwe Jungnickel, Königstein (DE);
Alexander Hilscher, Oberursel (DE);
Martin Simeth, Königstein (DE)

(73) Assignee: Braun GmbH, Kronberg (DE)

( * ) Notice: Subject to any disclaimer, the term of this patent is extended or adjusted under 35 U.S.C. 154(b) by 275 days.

(21) Appl. No.: 13/098,503

(22) Filed: May 2, 2011

(65) Prior Publication Data
US 2011/0265818 A1    Nov. 3, 2011

(30) Foreign Application Priority Data
May 3, 2010    (EP) .................................... 10004616

(51) Int. Cl.
*A61C 17/22*    (2006.01)

(52) U.S. Cl.
USPC .......................................................... 15/22.1

(58) Field of Classification Search
USPC .................................................. 15/22.1–29
See application file for complete search history.

(56) References Cited

U.S. PATENT DOCUMENTS

| | | | |
|---|---|---|---|
| 2007/0270221 A1 | 11/2007 | Park et al. | |
| 2008/0313829 A1 | 12/2008 | Dabrowski | |
| 2009/0143914 A1 | 6/2009 | Cook et al. | |

FOREIGN PATENT DOCUMENTS

| | | | |
|---|---|---|---|
| WO | 2007072430 | * | 6/2007 |
| WO | 2007122491 | * | 11/2007 |

OTHER PUBLICATIONS

International Search Report, date mailed Nov. 2, 2010, 5 pages.

* cited by examiner

*Primary Examiner* — Mark Spisich
(74) *Attorney, Agent, or Firm* — John P. Colbert; Vladimir Vitenberg

(57) ABSTRACT

An electric toothbrush is disclosed. The electric toothbrush includes at least one switch element and a control unit. The at least one switch element is operable by a user to switch the toothbrush to an on/off state, and operable by a user during the time that the at least one switch element is in its on state to select a brushing mode from a set of at least a first brushing mode and a second brushing mode. The control unit is arranged to control the electric toothbrush such that when the at least one switch element is operated to select a particular brushing mode in the on state, the toothbrush will then operate in that particular selected brushing mode when the at least one switch element is thereafter switched to an off state and then subsequently switched back to an on state, provided that the toothbrush was in the off state for a time period less than a threshold period (T).

10 Claims, 2 Drawing Sheets

ELECTRIC TOOTHBRUSH

CROSS REFERENCE TO RELATED APPLICATIONS

This application claims the benefit of European Patent Convention Application No. 10004616.8, filed May 3, 2010, the substance of which is incorporated by reference in its entirety herein.

FIELD OF THE INVENTION

The present disclosure relates to an electric toothbrush that is selectively operable in at least a first brushing mode and a second brushing mode.

BACKGROUND OF THE INVENTION

WO 2007/072430 A2 describes an electric toothbrush comprising a mode selection system that includes a first switch operable to control the ON/OFF condition of the toothbrush and a second switch operable when the first switch is in the OFF condition to select one of a plurality of possible modes of operation programmed in the toothbrush. A pre-established time is set during which the ON/OFF switch must be operated to an ON condition after the mode selection switch has been operated to select a particular mode. The described mode selection system has the disadvantage of being rather complex and non-automated.

Thus it is a desire to provide an electric toothbrush having several brushing modes that provides an improved handling.

SUMMARY OF THE INVENTION

In one embodiment, an electric toothbrush is provided. The electric toothbrush includes at least one switch element and a control unit. The at least one switch element is operable by a user to switch the toothbrush to an on/off state, and operable by a user during the time that the at least one switch element is in its on state to select a brushing mode from a set of at least a first brushing mode and a second brushing mode. The control unit is arranged to control the electric toothbrush such that when the at least one switch element is operated to select a particular brushing mode in the on state, the toothbrush will then operate in that particular selected brushing mode when the at least one switch element is thereafter switched to an off state and then subsequently switched back to an on state, provided that the toothbrush was in the off state for a time period less than a threshold period (T).

In another embodiment, a method of operating an electric toothbrush is provided. The method includes the steps of selecting during operation a brushing mode from the at least one of a first brushing mode and a second brushing mode; switching-off of the electric toothbrush; determining whether the electric toothbrush is in the off-state for a time period below a threshold period (T); switching-on of the electric toothbrush; and driving the electric toothbrush in the previously selected brushing mode if the off-time period is below the threshold period (T).

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
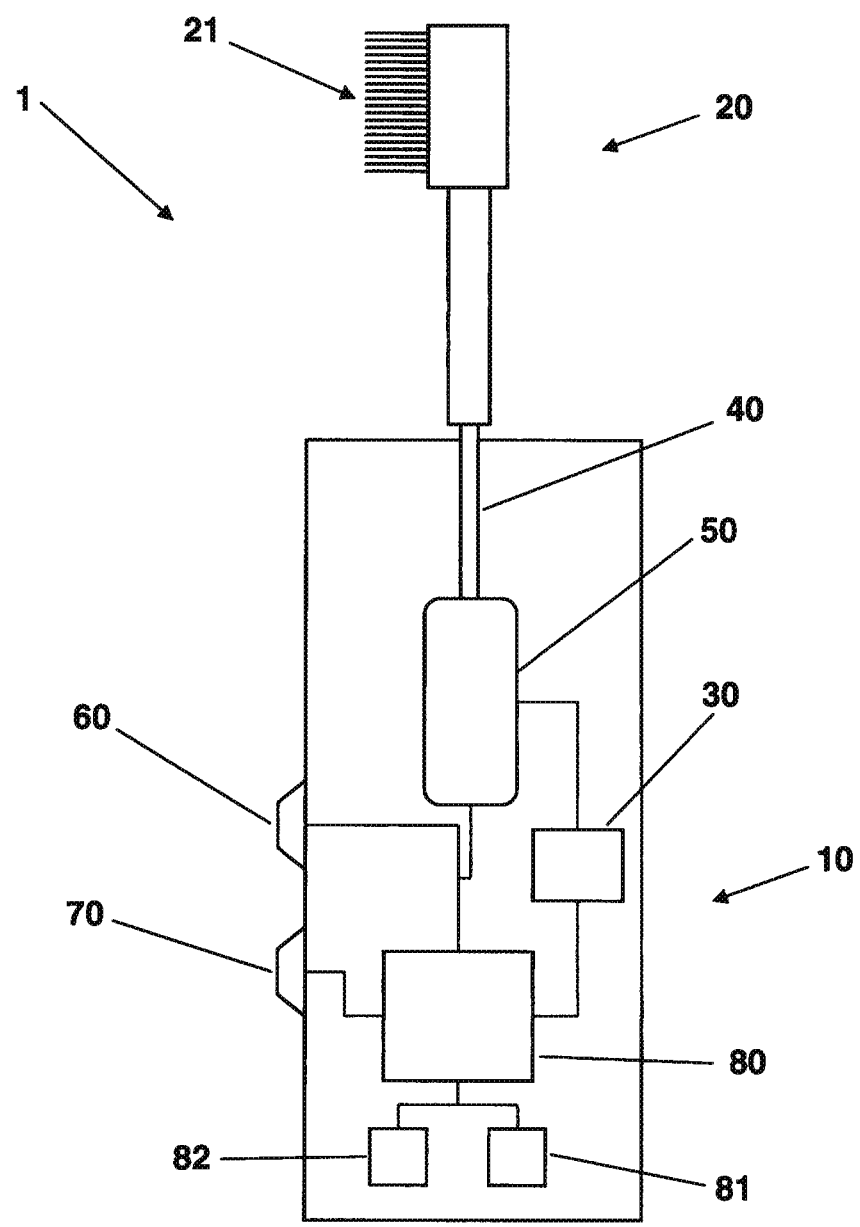
FIG. 1 is a schematic depiction of an electric toothbrush according to an embodiment shown and illustrated herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, an electric toothbrush has at least two different brushing modes, a first brushing mode and a second brushing mode, in which the electric toothbrush can be operated when being in the on-state. In one embodiment, the first brushing mode may be a regular cleaning mode, while the second brushing mode can be a massage mode or a deep cleaning mode. In another embodiment, the electric toothbrush may have further brushing modes, for example, a third brushing mode, which may be a sensitive cleaning mode. In one embodiment, the electric toothbrush has a control unit that is arranged to control the electric toothbrush in such a way that the electric toothbrush starts on a switch-on event with the previously selected brushing mode when the electric toothbrush had been in the off-state for a time period below a threshold period. In case the electric toothbrush had been in the off-state for a time period above a threshold period, then the control unit is arranged to start the electric toothbrush in a default brushing mode that is preselected from the at least first and second brushing modes.

In one embodiment, the electric toothbrush may comprise a head and a drive coupled to the head so that the head can be driven in the first or second brushing mode during operation of the electric toothbrush. The drive is then coupled to the control unit for controllably driving the head. The head may be a replacement brush that in its entirety is moved or the head may comprise a bristle carrier that is driven, for example, in an oscillatory rotating manner as is known in the art.

In an embodiment, the electric toothbrush as proposed comprises a memory unit for storing at least a parameter indicative of the previously selected brushing mode. The control unit may be arranged to store the parameter at the instant the user has selected the brushing mode or the storage may be delayed by a certain period or the parameter may be stored on a switching-off event.

In a further embodiment, the electric toothbrush comprises a timer unit for determining an off-time period while the electric toothbrush is in the off-state. The timer unit may determine the off-time period only until the off-time period equals the threshold period or the timer unit may continue to determine the off-time period as long as the electric toothbrush is in the off-state. The timer unit may in one embodiment be coupled with an energy source so as to be provided with energy as long as the timer unit fulfills its function, while in another embodiment the timer unit may be passive without coupling to an energy source. In the latter embodiment, the timer unit may be realized by an off-time determination capacitor having a calibrated leakage current.

The first and the second brushing modes may differ insofar as at least one of the frequency of the brushing motion or the amplitude of the brushing motion is different between the two brushing modes. Additionally or alternatively the numbers of degrees of freedom of the brushing motion may be different between the two brushing modes (for example, the first brushing mode may relate to an oscillatory-rotational motion while in the second brushing mode an additional poking motion is added). Instead of the before mentioned differences, the two brushing modes may differ insofar as, for example, one of the previously mentioned motion parameters has a different time dependency in the first and the second brushing mode.

In another embodiment, the threshold period is set to a value lying within the range of between about 1 second and about 36 hours. In an embodiment, the electric toothbrush includes a first switch element that is arranged for switching the electric toothbrush on or off and for selecting the brushing mode from the set of the first and second brushing modes. In another embodiment, a first switch element is arranged to switch on or off the electric toothbrush and a second switch element is arranged to select the brushing mode from the set of available brushing modes.

The present disclosure is also concerned with a method of operating an electric toothbrush, which method comprises the steps of:
- selecting during operation a brushing mode from the at least one of a first brushing mode and a second brushing mode;
- switching-off of the electric toothbrush;
- determining whether the electric toothbrush is in the off-state for a time period below a threshold period;
- switching-on of the electric toothbrush; and
- driving the electric toothbrush in the previously selected brushing mode if the off-time period is below the threshold period or otherwise driving the electric toothbrush in a default brushing mode preselected from the at least first and second brushing mode.

The method may include a step of storing a parameter indicative of the brushing mode used during active operation of the electric toothbrush. The parameter may be stored at the instant the brushing mode is selected or with some delay after the brushing mode was selected (for example, after 1 second or after 5 seconds) or the parameter may be stored on a switching-off event.

Turing to the figures, FIG. 1 is a schematic depiction of an exemplary embodiment of an electric toothbrush 1. The electric toothbrush 1 comprises a handle 10 and a head 20. A bristle field 21 is provided at the top of the head 20 for cleaning the teeth of a user. The handle 10 houses a motor 50 that is coupled to an energy source 30 and that is coupled to the head 20 via a shaft 40. The motor 50 and the shaft 40 may be coupled to each other via a gear section to e.g. transform a rotational movement of the motor 50 into an oscillatory rotational movement of the shaft 40. The motor 50 may be a DC motor or as a linear motor. During operation the motor 50 drives the head 20 in a brushing mode. Such arrangements are generally known.

A control unit 80 is coupled to the motor 50. The control unit 80 may be a microcontroller, an DSP or an ASIC (Application-Specific Integrated Circuit). The control unit 80 may integrally comprise a memory unit 81 and it may additionally or alternatively comprise a timer unit 82. In another embodiment, the memory unit 81 or the timer unit 82 is an individual component. The energy source 30 is here coupled to the control unit 80 to provide the control unit 80 with energy during operation.

A first switch element 60 is arranged to switch the electric toothbrush 1 on or off In the shown embodiment, a second switch element 70 is arranged as a brushing mode selector by which a user can selectively switch between the possible brushing modes of the electric toothbrush 1.

In one embodiment, the electric toothbrush 1 is arranged to have at least a first brushing mode and a second brushing mode, but the electric toothbrush 1 may have any other number of brushing modes above two. The first brushing mode may be a regular cleaning mode and the second brushing mode may be a massage mode, where the first and the second brushing modes are different to each other. The first brushing mode and the second brushing mode may in particular differ in the applied oscillatory frequency of the head motion, in the amplitude of the head motion, in the number of degrees of freedom of the head motion (for example, an additional poking motion may be superimposed on the oscillatory rotational motion, as is known in the art).

In one embodiment, the second brushing mode may have lower amplitude than the first brushing mode so that the massage mode is perceived as less aggressive than the regular cleaning mode. In another embodiment, the second brushing mode is a deep clean mode, which may differ from the first brushing mode by higher amplitude that is perceived as providing a more intense cleaning. The first brushing mode and the second brushing mode may in particular also differ in a time variation of one of the previously mentioned parameters, for example, the second brushing mode may provide a sinusoidal variation of the head motion amplitude instead of constant head motion amplitude used in the first brushing mode. The second switch element 70 can be used during operation to selectively switch between the brushing modes. In another embodiment, the electric toothbrush 1 comprises only a first switch element that is arranged to provide the functionality of an on/off switch and of a mode selector switch.

The timer unit 82 is arranged to determine whether the electric toothbrush is in an off state (the head 20 is not driven by the motor 50 in a brushing mode) for less than a preset threshold period. The timer unit 82 may hence be arranged to start counting down a timer value when the electric toothbrush is switched off The timer unit 82 may be connected to the energy source 30 in the off state of the electric toothbrush 1 to enable that the timer unit 82 is counting down the timer value until the timer reaches a value that indicates that the threshold period was reached. The timer unit 82 may then become disconnected from the energy source 30. In another embodiment, the timer unit 82 receives energy from a further energy source during the off state of the electric toothbrush 1. The further energy source may be, for example, a coin cell or as a double layer capacitor that provides enough energy so that the countdown of the timer value is enabled. The timer unit 82 may provide a high signal via an output as long as the countdown function is still active and a low signal in case the countdown function has stopped. In such an embodiment, the control unit 80 may only need to analyze the signal provided by the output of the timer unit 82 to decide on an on-switching event of the electric toothbrush 1 whether the period during which the electric toothbrush 1 was in the off-state is below the threshold period.

In another embodiment, the timer unit 82 determines the off-time as long as the electric toothbrush is switched off. The off-time value can then not only be used to compare the determined off-state period with the threshold period but it can also be used for informing the user about the time length of the off state. The threshold period may be chosen to lie in the range of for example, 1 second to 36 hours. A very short threshold period would avoid that an accidental switching-off of the electric toothbrush 1 would require that the user needs to select a favored brushing mode again when switching on the electric toothbrush 1 after a second or a few seconds. A short threshold period (for example, between about 10 seconds and about 120 seconds or about 240 seconds or about 600 seconds) may account for the usual short breaks a user makes during brushing (for example, to spit out toothpaste or to cough or to check the cleaning status, to respond to a phone call etc.). A long threshold period (for example, between about 1 hour and about 36 hours) may allow the user to always start in the favored brushing mode.

In another embodiment, the timer unit 82 may be realized by an off-time determination capacitor having a defined leakage current so that the voltage over this off-time determination capacitor changes with time in a defined way. Hence, assuming that the off-time determination capacitor can be loaded to full voltage within a short time so that at each switch-off event the load state of the off-time determination capacitor would always have a determined value, then the off-time period can be determined by comparing the voltage over the off-time determination capacitor at the next switch-on event. The behavior of the off-time determination capacitor can be calibrated a single time, for example prior to selling the electric toothbrush 1, or the electric toothbrush 1 may be arranged to calibrate this function itself after some time. The off-time determination capacitor would not require receiving energy during the off-state.

In one embodiment, the memory unit 81 may be a flash memory. A parameter may be stored in the memory unit 81 on a switch-off event that is indicative of the brushing mode used during the on-state. In case of two different brushing modes, a binary value may indicate the brushing mode in use. For example, a "0" stored in the memory unit 81 may indicate that the electric toothbrush 1 was in the first brushing mode when it was switched off and a "1" indicates that the electric toothbrush 1 was in the second brushing mode. In another embodiment, the respective parameter may be stored in the memory unit 81 already when a brushing mode is selected by the user. The storing of the parameter may be delayed by a certain period (for example, a delay of one second or a few seconds may be implemented) so that a random change in the selected brushing mode just very shortly before the electric toothbrush 1 is switched off is not considered.

Figure 2:
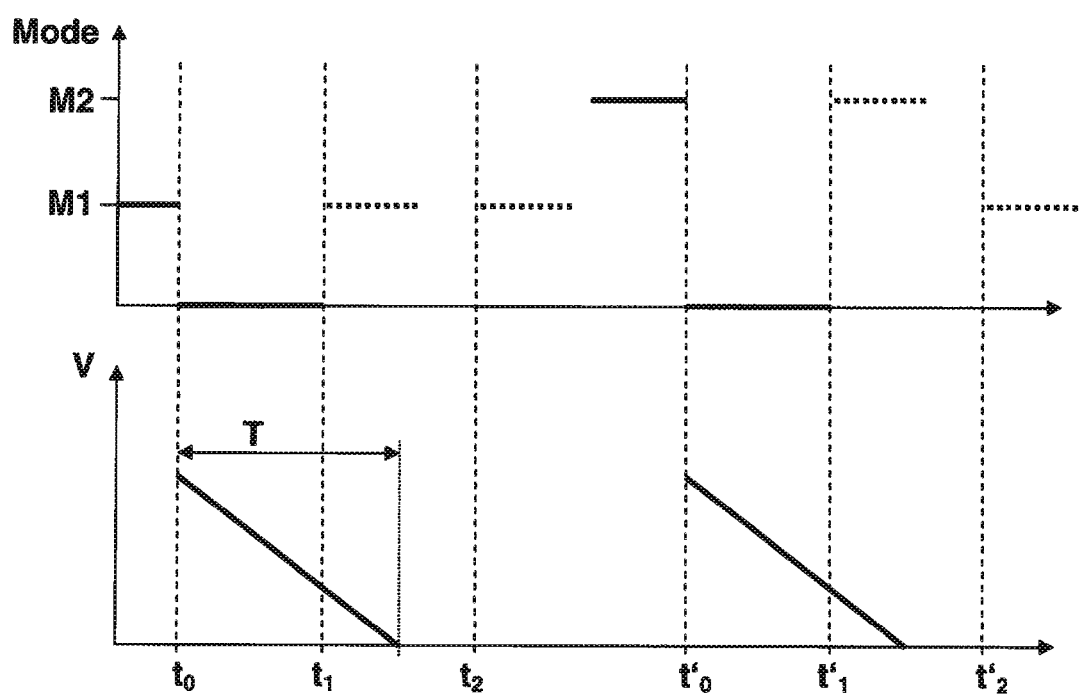
FIG. 2 is a split time diagram for the operation of an electric toothbrush according to an embodiment shown and illustrated herein.

Exemplary operation of a proposed electric toothbrush is described by reference to FIG. 2, which shows a split time diagram indicating the active brushing mode ("Mode") in the upper part of the diagram and the timer value ("V") in the lower part. Thus, FIG. 2 relates to an embodiment where a countdown timer is utilized. The electric toothbrush is operated in the first brushing mode (indicated by M1) for some time and is switched off at time $t_0$. When the electric toothbrush is switched off, the timer unit starts counting down the timer value V. In the shown embodiment, the timer value V would reach 0 when the electric toothbrush was in the off state for a period as long as the threshold period, which has a time length T. In case the electric toothbrush is switched on at time instant $t_1$ (where $t_1-t_0<T$), the electric toothbrush starts operation again in the first brushing mode M1 as it had been the previous brushing mode. In case the electric toothbrush is switched on at time instant $t_2$ (where $t_2-t_0>T$), the electric toothbrush also starts operation again in the first brushing mode M1, as the first brushing mode is here selected as the default brushing mode.

In the second example shown in the right hand part of the diagram, the electric toothbrush is operated for some time in the second brushing mode M2 before it is switched off at time instant $t'_0$. The timer unit then starts to count down the timer value V as in the first example. In case the electric toothbrush is switched on at time instant t1' (where t1'-t0'<T), the electric toothbrush starts operation again in the second brushing mode M2 as the electric toothbrush was in the off state for a time period lower than the threshold period T. In case the electric toothbrush is switched on at time instant $t'_2$ (where $t'_2-t'_0>T$), the electric toothbrush starts operation in the first brushing mode M1, as the first brushing mode M1 is here selected as the default brushing mode, which will be used in case the off-state period was longer than the threshold period T.

A method of operating an electric toothbrush as proposed may in particular comprise the steps of: (a) setting a default brushing mode for driving a head portion of the electric toothbrush selected from a set of at least a first brushing mode and a second brushing mode (this may be an initial step performed before the electric toothbrush is sold, but the electric toothbrush may also be arranged to allow setting a default brushing mode by the user); (b) selecting a brushing mode during operation in which the head portion of the electric toothbrush is driven from the set of at least the first brushing mode and the second brushing mode; (c) storing a parameter indicative of the selected brushing mode; (d) switching the electric toothbrush into an off state (step (c) may happen in particular prior to the switching-off event or it may happen at the switching-off event); (e) determining whether the electric toothbrush is kept in the off-state for a time period below a threshold period; (f) switching the electric toothbrush into the on state; and (g) driving the head portion in the mode indicated by the stored parameter if the off-state period is below the threshold period or otherwise in the default brushing mode.

In the present disclosure, the term "electric toothbrush" stands synonymously for oral hygiene devices and the term "brushing mode" stands synonymously for active operation modes of the oral hygiene device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An electric toothbrush comprising:
   at least one switch element operable by a user to switch the toothbrush to an on/off state, and operable by a user during the time that the at least one switch element is in its on state to select a brushing mode from a set of at least a first brushing mode and a second brushing mode; and
   a control unit arranged to control the electric toothbrush such that when the at least one switch element is operated to select a particular brushing mode in the on state, the toothbrush will then operate in that particular selected brushing mode when the at least one switch element is thereafter switched to an off state and then subsequently switched back to an on state, provided that the toothbrush was in the off state for a time period less than a threshold period (T), wherein the brushing mode is selectable during the on state.

2. The electric toothbrush according to claim 1, further comprising a head and a drive for driving the head, the drive being coupled to the control unit.

3. The electric toothbrush according to claim 2, wherein the first brushing mode and the second brushing mode differ in at least one of the amplitude of the movement of the head, the frequency of the movement of the head, the number of degrees of freedom of the movement of the head, or a time-dependent variation of at least one of the mentioned parameters.

4. The electric toothbrush according to claim 2, wherein the control unit is arranged to control the drive to drive the head portion in at least three different brushing modes.

5. The electric toothbrush according to claim 1, further comprising a memory unit for storing at least a parameter indicative of the selected brushing mode.

6. The electric toothbrush according to claim 1, further comprising a timer unit for determining the off-time period during which the electric toothbrush is in the off state.

7. The electric toothbrush according to claim 6, wherein the timer unit is provided with energy from an energy source in an off-state of the electric toothbrush at least during the threshold period (T).

8. The electric toothbrush according to claim 1, wherein the threshold period (T) is in the range of from about 1 second to about 36 hours.

9. The electric toothbrush according to claim 1, wherein the at least one switch element includes a first switch element and a second switch element.

10. The electric toothbrush according to claim 9, wherein the first switch element is operable by a user to switch the toothbrush to an on/off state and the second switch element is operable by a user during the time that the at least one switch element is in its on state to select a brushing mode from a set of at least a first brushing mode and a second brushing mode.

* * * * *